(12) United States Patent
Francotte et al.

(10) Patent No.: US 7,268,129 B2
(45) Date of Patent: Sep. 11, 2007

(54) FLUORINATED BENZOTHIADIAZINE COMPOUNDS

(75) Inventors: Pierre Francotte, Liege (BE); Pierre Fraikin, Dison (BE); Pascal De Tullio, Jupille (BE); Bernard Pirotte, Oupeye (BE); Pierre Lestage, La Celle Saint Cloud (FR); Laurence Danober, Montesson (FR); Daniel-Henri Caignard, Le Pecq (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 304 days.

(21) Appl. No.: 11/041,495

(22) Filed: Jan. 24, 2005

(65) Prior Publication Data

US 2005/0165008 A1 Jul. 28, 2005

(51) Int. Cl.
*C07D 285/22* (2006.01)
*A61K 31/5415* (2006.01)
*A61P 25/24* (2006.01)

(52) U.S. Cl. ..................... 514/223.2; 544/12
(58) Field of Classification Search .................. 544/12; 514/223.2
See application file for complete search history.

(56) References Cited

OTHER PUBLICATIONS

Alt et al. Current Pharmaceutical Design, 2005, 11, 1511-1527.*
Black et al Psychopharmacology (2005) 179: 154-163.*

\* cited by examiner

*Primary Examiner*—Kahsay Habte
(74) *Attorney, Agent, or Firm*—Hueschen and Sage

(57) ABSTRACT

Compounds of formula (I):

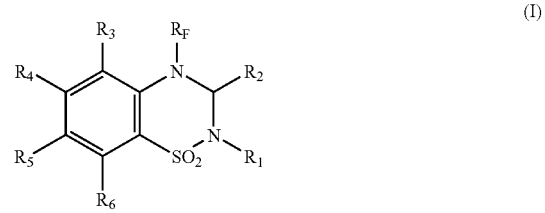

wherein:

$R_F$ represents monofluoro- or polyfluoro-alkyl or monofluoro- or polyfluoro-cycloalkylalkyl, $R_1$ represents hydrogen or a group selected from alkylaminocarbonyl and optionally substituted alkyl, $R_2$ represents hydrogen, halogen or a group selected from cycloalkyl and optionally substituted alkyl, $R_3$ to $R_6$, which may be the same or different, each represent an atom or group selected from hydrogen, halogen, nitro, cyano, alkylsulphonyl, hydroxy, alkoxy, optionally substituted alkyl and optionally substituted amino, its optical isomers when they exist, and also their addition salts with a pharmaceutically acceptable acid or base.

Medicinal products containing the same which are useful as AMPA modulators.

18 Claims, No Drawings

FLUORINATED BENZOTHIADIAZINE COMPOUNDS

BACKGROUND OF THE INVENTION

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral reviews, 1992, 16, 13-24; Progress in Neurobiology, 1992, 39, 517-545).

In addition, certain works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

Benzothiadiazine compounds have been described as modulators of AMPA receptors in patent applications WO 98/12185 and WO 01/40210.

The synthesis of new compounds which are modulators of AMPA receptors has been especially valuable for increasing the potency, selectivity and bioavailability of the compounds already described.

DETAILED DESCRIPTION OF THE INVENTION

More specifically, the present invention relates to compounds of formula (I):

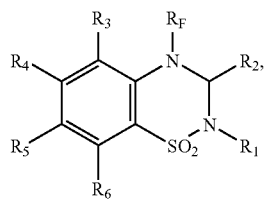

(I)

wherein:
$R_F$ represents a linear or branched monofluoro- or polyfluoro-$C_1$-$C_6$alkyl group or a monofluoro- or polyfluoro-cycloalkylalkyl group wherein the alkyl moiety is $C_1$-$C_6$ and linear or branched and the cycloalkyl moiety is $C_3$-$C_7$,
$R_1$ represents a hydrogen atom or a group selected from linear or branched $C_1$-$C_6$alkyl optionally substituted by one or more halogen atoms, preferably fluorine, and from linear or branched $C_1$-$C_6$alkylaminocarbonyl,
$R_2$ represents a hydrogen or halogen atom or a group selected from linear or branched $C_1$-$C_6$alkyl optionally substituted by one or more halogen atoms, and from $C_3$-$C_7$cycloalkyl,
$R_3$, $R_4$, $R_5$ and $R_6$, which may be the same or different, each represent an atom or group selected from hydrogen and halogen atoms and the groups nitro, cyano, linear or branched $C_1$-$C_6$alkylsulphonyl, hydroxy, linear or branched $C_1$-$C_6$alkoxy, linear or branched $C_1$-$C_6$alkyl optionally substituted by one or more halogen atoms, and amino optionally substituted by one or two linear or branched $C_1$-$C_6$alkyl groups, and also to their addition salts with a pharmaceutically acceptable acid or base, and optical isomers thereof when they exist, it being understood that $R_3$ represents a hydrogen atom when $R_6$ does not represent a hydrogen atom.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

Among the pharmaceutically acceptable bases there may be mentioned, without implying any limitation, sodium hydroxide, potassium hydroxide, triethylamine, tert-butylamine.

Preferred $R_F$ groups are linear or branched monofluoro-$C_1$-$C_6$alkyl groups, and more especially the groups fluoromethyl, 2-fluoroethyl, 3-fluoropropyl and 4-fluorobutyl. Preferred polyfluoroalkyl groups are the groups 2,2-difluoroethyl and 2,2,2-trifluoroethyl.

$R_1$, $R_2$ and $R_3$ preferably each represent a hydrogen atom.

When $R_2$ represents a halogen atom, it preferably represents a fluorine atom.

$R_4$ and $R_6$ preferably each represent a hydrogen or halogen atom.

$R_5$ preferably represents a halogen atom.

Greater preference is given to compounds wherein $R_4$ represents a hydrogen atom and $R_5$ represents a halogen atom and to compounds wherein $R_4$ and $R_5$ each represent a halogen atom.

Preferred compounds according to the invention are:
7-chloro-4-(2-fluoroethyl)-3,4-dihydro-2H-1,2,4-benzothiadiazine 1,1-dioxide,
6,7-dichloro-4-(2-fluoroethyl)-3,4-dihydro-2H-1,2,4-benzothiadiazine 1,1-dioxide,
6-chloro-7-fluoro-4-(2-fluoroethyl)-3,4-dihydro-2H-1,2,4-benzothiadiazine 1,1-dioxide, and
6-chloro-7-bromo-4-(2-fluoroethyl)-3,4-dihydro-2H-1,2,4-benzothiadiazine 1,1-dioxide.

The invention relates also to a process for the preparation of compounds of formula (I), starting from the compound of formula (II):

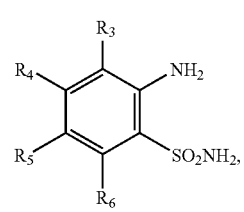

(II)

wherein $R_3$, $R_4$, $R_5$ and $R_6$ are as defined for formula (I),
which is cyclised in the presence of a compound of formula (III):

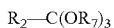 (III), wherein $R_2$ is as defined for formula (I) and $R_7$ represents a linear or branched $C_1$-$C_6$alkyl group,
to yield the compound of formula (IV):

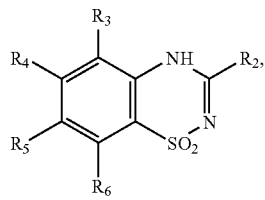 (IV)

wherein $R_2$, $R_3$, $R_4$, $R_5$ and $R_6$ are as defined hereinbefore,
which is reacted with a compound of formula (V):

 (V), wherein $R_F$ is as defined for formula (I) and X represents a leaving group selected from iodine and bromine atoms and tosylate, mesylate and triflate groups,
to yield the compound of formula (VI):

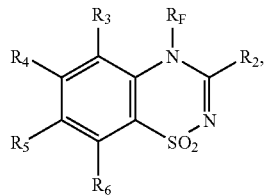 (VI)

wherein $R_2$, $R_3$, $R_4$, $R_5$, $R_6$ and $R_F$ are as defined hereinbefore,
which is reacted with a reducing agent to yield the compound of formula (Ia), a particular case of the compounds of formula (I) wherein $R_1$ represents a hydrogen atom:

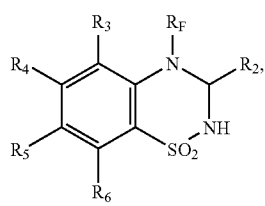 (Ia)

wherein $R_2$, $R_3$, $R_4$, $R_5$, $R_6$ and $R_F$ are as defined hereinbefore,
which compound of formula (Ia), when it is desired to obtain compounds of formula (I) wherein $R_1$ represents an optionally substituted alkyl group,
is reacted with a compound of formula (VII):

 (VII), wherein $R'_1$ represents a linear or branched $C_1$-$C_6$alkyl group optionally substituted by one or more halogen atoms and X represents a leaving group selected from iodine and bromine atoms and tosylate, mesylate and triflate groups, to yield the compound of formula (Ib):

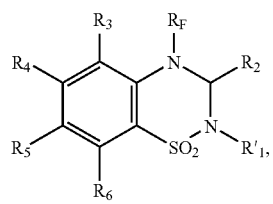 (Ib)

wherein $R_2$, $R_3$, $R_4$, $R_5$, $R_6$, $R_F$ and $R'_1$ are as defined hereinbefore,
or which compound of formula (Ia), when it is desired to obtain compounds of formula (I) wherein $R_1$ represents an alkylaminocarbonyl group,
is reacted with a compound of formula (VIII);

 (VIII), wherein $R_8$ represents a linear or branched $C_1$-$C_6$alkyl group,
to yield the compound of formula (Ic):

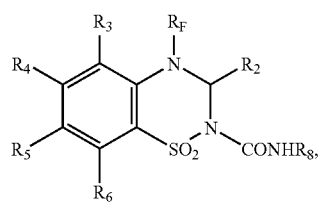 (Ic)

wherein $R_2$, $R_3$, $R_4$, $R_5$, $R_6$, $R_F$ and $R_8$ are as defined hereinbefore,
the compounds of formula (Ia), (Ib) and (Ic) constituting the totality of the compounds of formula (I).

The compound of formula (II) can be obtained either by the process described by Girard et al. (J. Chem. Soc. Perkin I 1979, 1043-1047) or by chlorosulphonation of an appropriate aniline using chlorosulphonic acid, followed by conversion of the resulting sulphonyl chloride into the corresponding sulphonamide using ammonium hydroxide.

The compounds of formula (VI) are new and, by virtue of their being intermediates for the synthesis of compounds of formula (I), also form part of the invention.

The compounds of formula (VIa), a particular case of the compounds of formula (VI) wherein RF represents a monofluoro- or polyfluoro-$C_2$-$C_6$alkyl group:

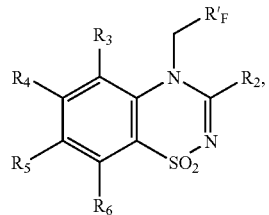 (VIa)

wherein $R_2$, $R_3$, $R_4$, $R_5$ and $R_6$ are as defined for formula (I) and $R'_F$ represents a monofluoro- or polyfluoro-$C_1$-$C_5$alkyl group, can also be prepared by acylation of the compound of formula (II) in the presence of a compound of formula (IX):

R'<sub>F</sub>—COCl    (IX), wherein R'<sub>F</sub> is as defined hereinbefore,
to yield the compound of formula (X):

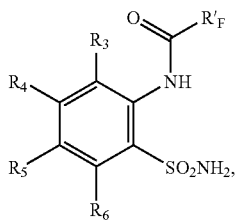

wherein $R_3$, $R_4$, $R_5$, $R_6$ and R'<sub>F</sub> are as defined hereinbefore, which is reacted with lithium aluminium hydride to yield the compound of formula (XI):

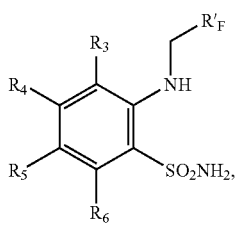

wherein $R_3$, $R_4$, $R_5$, $R_6$ and R'<sub>F</sub> are as defined hereinbefore, which is cyclised in the presence of a compound of formula (III) to yield the compound of formula (VIa).

The compounds of the present invention have AMPA receptor-activating properties which make them of use in the treatment or prevention of disorders of memory and cognition that are associated with age, with syndromes of anxiety or depression, with progressive neurodegenerative diseases, with Alzheimer's disease, with Parkinson's disease, with Pick's disease, with Huntington's chorea, with Korsakoff's disease, with schizophrenia, with the sequelae of acute neurodegenerative diseases, with frontal lobe and subcortical dementias, with the sequelae of ischaemia and with the sequelae of epilepsy.

The invention relates also to pharmaceutical compositions comprising, as active ingredient, at least one compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations and drinkable suspensions.

The useful dosage can be varied according to the nature and severity of the disorder, the administration route and the age and weight of the patient and ranges from 0.01 to 500 mg per day in one or more administrations.

The Examples that follow illustrate the invention.

The starting materials used are products that are known or that are prepared according to known operating procedures.

The structures of the compounds described in the Examples were determined according to the usual spectrophotometric techniques (infrared, NMR, mass spectrometry).

EXAMPLE 1

7-Chloro-4-(2-fluoroethyl)-3,4-dihydro-2H-1,2,4-benzothiadiazine 1,1-dioxide

Step A: 7-Chloro-4H-1,2,4-benzothiadiazine 1,1-dioxide 40 ml of ethyl orthoformate are added to 4.75 g of 2-amino-5-chlorobenzenesulphonamide, the preparation of which is described in the journal J. Chem. Soc. Perkin I 1979, 1043-1047. The mixture is heated at 110° C. for 30 minutes in an open vessel. Dissolution is observed, and then the appearance of a precipitate.

The volume of the reaction mixture is then reduced by half under reduced pressure. The precipitate obtained is collected by filtration and is then washed with ether and dried to yield the expected compound in the form of white crystals in a yield of from 85 to 90%.

Melting point: 243-244° C.

Step B: 7-Chloro-4-(2-fluoroethyl)-4H-1,2,4-benzothiadiazine 1,1-dioxide 600 mg of the compound obtained in the previous Step are dissolved with the aid of heat in 15 ml of acetonitrile; 1.2 g of potassium carbonate and 0.6 ml of 1-fluoro-2-iodoethane are then added and the reaction mixture is heated at 70° C. in a hermetically closed vessel, with stirring, for 30 hours. The solvents are then removed under reduced pressure. The solid residue thereby obtained is taken up in 5 ml of water and is immediately collected on a filter. The contents of the filter are washed several times with water, dried and then suspended in a minimum of ethyl acetate and collected on a filter. The powder thereby obtained is recrystallised from warm acetone to yield the title compound in a yield of 75-80%.

Melting point: 211-218° C.

Step C: 7-Chloro-4-(2-fluoroethyl)-3,4-dihydro-2H-1,2,4-benzothiadiazine 1,1-dioxide To 500 mg of the compound obtained in the previous Step, dissolved in 25 ml of isopropanol, there are added 750 mg of sodium borohydride and the mixture is then heated at 50° C. for 40 minutes. The solvent is then removed under reduced pressure; the residue obtained is then taken up in 10 ml of water, cooled in an ice bath and adjusted to pH=5 by adding concentrated hydrochloric acid. After extraction with chloroform, the combined organic phases are dried, filtered and evaporated, and the residue obtained is crystallised from methanol to yield, after filtration and then drying, the expected compound in a yield of 85%.

Melting point: 120-121° C.

EXAMPLE 2

7-Chloro-4-(2-fluoroethyl)-2-methyl-3-4-dihydro-2H-1,2,4-benzothiadiazine 1,1-dioxide 360 mg of the compound of Example 1 are introduced into 8 ml of acetonitrile. 600 mg of potassium carbonate are then added, and also 0.5 ml of methyl iodide. The solution is heated at 55° C. for 5 hours. The solvent is then removed under reduced pressure and the residue is suspended in 5 ml of water. The insoluble material is collected by filtration, washed with water and then dried. The residue is then recrystallised from methanol with the aid of heat. After cooling, the precipitate obtained is collected by filtration, washed with a minimum of cold methanol and dried to yield the expected compound.

Melting point: 112-114° C.

EXAMPLE 3

7-Fluoro-4-(2-fluoroethyl)-3,4-dihydro-2H-1,2,4-benzothiadiazine 1,1-dioxide

Step A: 2-Amino-5-fluorobenzenesulphonamide

The expected compound is obtained, starting from 4-fluoroaniline, in accordance with the procedure described in J. Chem. Soc. Perkin. I 1979, 1043-1047.

Step B: 7-Fluoro-4-(2-fluoroethyl)-4H-1,2,4-benzothiadiazine 1,1-dioxide

The expected compound is obtained according to the procedure described in Steps A and B of Example 1, starting from the compound obtained in the previous Step.

Melting point: 197-198° C.

Step C: 7-Fluoro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 133-134° C.

EXAMPLE 4

6,7-Dichloro-4-(2-fluoroethyl)-3,4-dihydro-2H-1,2,4-benzothiadiazine 1,1-dioxide Step A: 2-Amino-4,5-dichlorobenzenesulphonamide The expected compound is obtained, starting from 3,4-dichloroaniline, by chlorosulphonation according to the procedure described in J. Med. Chem. 1971, 15, 118-120, followed by conversion of the resulting sulphonyl chloride into the sulphonamide with the aid of ammonium hydroxide.

Step B: 6,7-Dichloro-4-(2-fluoroethyl)-4H-1,2,4-benzothiadiazine 1,1-dioxide

The expected compound is obtained according to the procedure described in Steps A and B of Example 1, starting from the compound obtained in the previous Step.

Melting point: 233-234° C.

Step C: 6,7-Dichloro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 156-157° C.

EXAMPLE 5

6-Chloro-7-fluoro-4-(2-fluoroethyl)-3,4-dihydro-2H-1,2,4-benzothiadiazine 1,1-dioxide Step A: 6-Chloro-7-fluoro-4-(2-fluoroethyl)-4H-1,2,4-benzothiadiazine 1,1-dioxide The expected compound is obtained according to the procedure described in Steps A and B of Example 4, starting from 3-chloro-4-fluoroaniline.

Melting point: 195-196° C.

Step B: 6-Chloro-7-fluoro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 183-184° C.

EXAMPLE 6

6-Chloro-4-(2-fluoroethyl)-3,4-dihydro-2H-1,2,4-benzothiadiazine 1,1-dioxide

Step A: 6-Chloro-4-(2-fluoroethyl)-4H-1,2,4-benzothiadiazine 1,1-dioxide

The expected compound is obtained according to the procedure described in Steps A and B of Example 3, starting from 3-chloroaniline.

Melting point: 182-184° C.

Step B: 6-Chloro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 171-175° C.

EXAMPLE 7

6-Fluoro-4-(2-fluoroethyl)-3,4-dihydro-2H-1,2,4-benzothiadiazine 1,1-dioxide

Step A: 6-Fluoro-4-(2-fluoroethyl)-4H-1,2,4-benzothiadiazine 1,1-dioxide

The expected compound is obtained according to the procedure described in Steps A and B of Example 3, starting from 3-fluoroaniline.

Melting point: 155-160° C.

Step B: 6-Fluoro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 107-109° C.

EXAMPLE 8

7-Bromo-6-chloro-4-(2-fluoroethyl)-3,4-dihydro-2H-1,2,4-benzothiadiazine 1,1-dioxide Step A: 7-Bromo-6-chloro-4-(2-fluoroethyl)-4H-1,2,4-benzothiadiazine 1,1-dioxide The expected compound is obtained according to the procedure described in Steps A and B of Example 4, starting from 4-bromo-3-chloroaniline.

Melting point: 219-224° C.

Step B: 7-Bromo-6-chloro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 159-162° C.

EXAMPLE 9

4-(2-Fluoroethyl)-7-methyl-3,4-dihydro-2H-1,2,4-benzothiadiazine 1,1-dioxide Step A: 4-(2-Fluoroethyl)-7-methyl-4H-1,2,4-benzothiadiazine 1,1-dioxide The expected compound is obtained according to the procedure described in Steps A and B of Example 1, starting from 2-amino-5-methylbenzenesulphonamide, the preparation of which is described in J. Chem. Soc. Perkin I 1979, 1043-1047.

Melting point: 179-184° C.

Step B: 4-(2-Fluoroethyl)-7-methyl-3,4-dihydro-2H-1,2,4-benzothiadiazine 1,1-dioxide The expected compound is obtained according to the procedure described in Step C of Example 1, starting from the compound obtained in the previous Step.

Melting point: 88-90° C.

EXAMPLE 10

7-Chloro-4-(4-fluorobutyl)-3,4-dihydro-2H-1,2,4-benzothiadiazine 1,1-dioxide Step A: 7-Chloro-4-(4-fluorobutyl)-4H-1,2,4-benzothiadiazine 1,1-dioxide 150 mg of the compound obtained in Step A of Example 1 are dissolved in 8 ml of acetonitrile, to which 300 mg of $K_2CO_3$ and 0.15 ml of 1-bromo-4-fluorobutane are added. The reaction mixture is introduced into a sealed autoclave and is heated at 100° C. for 3 hours. After cooling, the solvent is evaporated off under reduced pressure and the residue is taken up in a minimum of water. The insoluble material is collected by filtration, washed with water and dried. The precipitate is then recrystallised from a minimum of ethyl acetate with the aid of heat. After cooling, the title compound is collected by filtration, washed with a minimum of ethyl acetate and dried.

Melting point: 135-138° C.

Step B: 7-Chloro-4-(4-fluorobutyl)-3,4-dihydro-2H-1,2,4-benzothiadiazine 1,1-dioxide The expected compound is obtained according to the procedure described in Step C of Example 1, starting from the compound obtained in the previous Step.

Melting point: 154-156° C.

EXAMPLE 11

6,8-Dichloro-4-(2-fluoroethyl)-3,4-dihydro-2H-1,2,4-benzothiadiazine 1,1-dioxide Step A: 6,8-Dichloro-4-(2-fluoroethyl)-4H-1,2,4-benzothiadiazine 1,1-dioxide The expected compound is obtained according to the procedure described in Steps A and B of Example 3, starting from 3,5-dichloroaniline.

Step B: 6,8-Dichloro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 180-184° C.

EXAMPLE 12

7-Chloro-4-(3-fluoropropyl)-3,4-dihydro-2H-1,2,4-benzothiadiazine 1,1-dioxide Step A: 7-Chloro-4-(3-fluoropropyl)-4H-1,2,4-benzothiadiazine 1,1-dioxide The expected compound is obtained according to the procedure described in Step A of Example 10, replacing the 1-bromo-4-fluorobutane by 1-bromo-3-fluoropropane.

Melting point: 209-212° C.

Step B: 7-Chloro-4-(3-fluoropropyl)-3,4-dihydro-2H-1,2,4-benzothiadiazine 1,1-dioxide The expected compound is obtained according to the procedure described in Step C of Example 1, starting from the compound obtained in the previous Step.

Melting point: 143-145° C.

EXAMPLE 13

7-Chloro-4-(fluoromethyl)-3,4-dihydro-2H-1,2,4-benzothiadiazine 1,1-dioxide

Step A: 7-Chloro-4-(fluoromethyl)-4H-1,2,4-benzothiadiazine 1,1-dioxide

The expected compound is obtained according to the procedure described in Step A of Example 10, replacing the 1-bromo-4-fluorobutane by bromofluoromethane.

Melting point: 227-232° C.

Step B: 7-Chloro-4-(fluoromethyl)-3,4-dihydro-2H-1,2,4-benzothiadiazine 1,1-dioxide The expected compound is obtained according to the procedure described in Step C of Example 1, starting from the compound obtained in the previous Step.

EXAMPLE 14

7-Bromo-4-(2-fluoroethyl)-3,4-dihydro-2H-1,2,4-benzothiadiazine 1,1-dioxide

Step A: 7-Bromo-4-(2-fluoroethyl)-4H-1,2,4-benzothiadiazine 1,1-dioxide

The expected compound is obtained according to the procedure described in Steps A and B of Example 3, starting from 4-bromoaniline.

Melting point: 229-232° C.

Step B: 7-Bromo-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 122-124° C.

EXAMPLE 15

7-Iodo-4-(2-fluoroethyl)-3,4-dihydro-2H-1,2,4-benzothiadiazine 1,1-dioxide

Step A: 7-Iodo-4-(2-fluoroethyl)-4H-1,2,4-benzothiadiazine 1,1-dioxide

The expected compound is obtained according to the procedure described in Steps A and B of Example 3, starting from 4-iodoaniline.

Melting point: 220-223° C.

Step B: 7-Iodo-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 156-158° C.

EXAMPLE 16

4-(2-Fluoroethyl)-7-nitro-3,4-dihydro-2H-1,2,4-benzothiadiazine 1,1-dioxide

Step A: 4-(2-Fluoroethyl)-7-nitro-4H-1,2,4-benzothiadiazine 1,1-dioxide

The expected compound is obtained according to the procedure described in Steps A and B of Example 3, starting from 4-nitroaniline.

Step B: 4-(2-Fluoroethyl)-7-nitro-3,4-dihydro-2H-1,2,4-benzothiadiazine 1,1-dioxide The expected compound is obtained according to the procedure described in Step C of Example 1, starting from the compound obtained in the previous Step.

Melting point: 165-166° C.

EXAMPLE 17

7-Nitro-4-(2,2,2-trifluoroethyl)-3,4-dihydro-2H-1,2,4-benzothiadiazine 1,1-dioxide Step A: 7-Nitro-4-(2,2,2-trifluoroethyl)-4H-1,2,4-benzothiadiazine 1,1-dioxide The expected compound is obtained according to the procedure described in Steps A and B of Example 3, starting from 4-nitroaniline and 1,1,1-trifluoro-2-iodoethane.

Step B: 7-Nitro-4-(2,2,2-trifluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 191-193° C.

EXAMPLE 18

7-Chloro-4-(2,2-difluoroethyl)-3,4-dihydro-2H-1,2,4-benzothiadiazine 1,1-dioxide Step A: 5-Chloro-2-(2,2-difluoroacetamido)benzenesulphonamide To 1 g of 2-amino-5-chlorobenzenesulphonamide (obtained in accordance with J. Chem. Soc. Perkin I 1979, 1043-1047) dissolved in 4 ml of dioxane there are added, in the cold state (+5° C.), 0.6 ml of pyridine and 0.6 ml of difluoroacetic acid chloride. The flask is hermetically closed immediately and subjected to vigorous stirring at ambient temperature for 10 minutes. The solvents are then removed under reduced pressure. The solid residue is taken up in water (12 ml), and the insoluble material is collected by filtration, washed with water and dried to yield the expected compound.

Melting point: 180-181° C.

Step B: 5-Chloro-2-(2,2-difluoroethylamino)benzenesulphonamide 1 g of the compound obtained in the previous Step is suspended in 15 ml of dry ether; 500 mg of LiAlH$_4$ are added thereto. The mixture is stirred. After 30 minutes, the mixture is cooled in an ice bath and water is slowly added; the mixture is then acidified to pH 4 by adding concentrated HCl. The mixture is extracted with ethyl acetate; the organic phases are dried, removed under reduced pressure. The dry residue is then recrystallised from a mixture of acetone/water (1:10).

Melting point: 127-131° C.

Step C: 7-Chloro-4-(2,2-difluoroethyl)-4H-1,2,4-benzothiadiazine 1,1-dioxide 300 mg of the compound obtained in the previous Step are suspended in 1.5 ml of ethyl orthoformate. The mixture is heated at 180° C. in an open vessel for 45 minutes. After cooling, the insoluble material which appears is collected by filtration and washed several times with diethyl ether and dried.

Melting point: 183-186° C.

Step D: 7-Chloro-4-(2,2-difluoroethyl)-3,4-dihydro-2H-1,2,4-benzothiadiazine 1,1-dioxide 250 mg of the compound obtained in the previous Step are dissolved with the aid of heat in 15 ml of isopropanol. 370 mg of finely broken-up NaBH$_4$ are added to the solution, which is then heated at 60° C. for 20 minutes. The solvent is then evaporated off under reduced pressure and the residue is taken up in 10 ml of water. The suspension obtained is adjusted to pH 5 with the aid of 6N HCl and is extracted 3 times with chloroform. The organic phase is dried over magnesium sulphate and evaporated under reduced pressure. The residue is then recrystallised from methanol with the aid of heat. After cooling, the precipitate obtained is collected by filtration, washed with cold methanol and dried.

Melting point: 126-128° C.

EXAMPLE 19

6,7-Difluoro-4-(2-fluoroethyl)-3,4-dihydro-2H-1,2,4-benzothiadiazine 1,1-dioxide Step A: 6,7-Difluoro-4-(2-fluoroethyl)-4H-1,2,4-benzothiadiazine 1,1-dioxide The expected compound is obtained according to the procedure described in Steps A and B of Example 3, starting from 3,4-difluoroaniline.

Melting point: 198-202° C.

Step B: 6,7-Difluoro-4-(2-fluoroethyl)-3,4-dihydro-2H-1,2,4-benzothiadiazine 1,1-dioxide The expected compound is obtained according to the procedure described in Step C of Example 1, starting from the compound obtained in the previous Step.

Melting point: 128-130° C.

EXAMPLE 20

7-Chloro-2-ethylaminocarbonyl-4-(2-fluoroethyl)-3,4-dihydro-2H-1,2,4-benzothiadiazine 1,1-dioxide To 500 mg of the compound of Example 1 dissolved in 2.5 ml of acetonitrile there are added 0.5 ml of triethylamine and 2.5 ml of ethyl isocyanate. The reaction mixture is stirred at ambient temperature for 5 hours. The solvent is then removed under reduced pressure. The residue is taken up in 10 ml of acetone; charcoal is added to the resulting solution, which is then filtered; water is then added to the filtrate. The precipitate obtained is collected by filtration, washed with water and dried.

Melting point: 138-140° C.

EXAMPLE 21

6,7-Dichloro-4-(3-fluoropropyl)-3,4-dihydro-2H-1,2,4-benzothiadiazine 1,1-dioxide Step A: 6,7-Dichloro-4H-1,2,4-benzothiadiazine 1,1-dioxide The expected compound is obtained according to the procedure described in Step A of Example 1, starting from the compound obtained in Step A of Example 4.

Step B: 6,7-Dichloro-4-(3-fluoropropyl)-4H-1,2,4-benzothiadiazine 1,1-dioxide

The expected compound is obtained according to the procedure described in Step A of Example 12, starting from the compound obtained in the previous Step.

Step C: 6,7-Dichloro-4-(3-fluoropropyl)-3,4-dihydro-2H-1,2,4-benzothiadiazine 1,1-dioxide The expected compound is obtained according to the procedure described in Step C of Example 1, starting from the compound obtained in the previous Step.

Melting point: 180-182° C.

EXAMPLE 22

6,7-Dichloro-4-(4-fluorobutyl)-3,4-dihydro-2H-1,2,4-benzothiadiazine 1,1-dioxide Step A: 6,7-Dichloro-4-(4-fluorobutyl)-4H-1,2,4-benzothiadiazine 1,1-dioxide The expected compound is obtained according to the procedure described in Step A of Example 10, starting from the compound obtained in Step A of Example 21.

Step B: 6,7-Dichloro-4-(4-fluorobutyl)-3,4-dihydro-2H-1,2,4-benzothiadiazine 1,1-dioxide The expected compound is obtained according to the procedure described in Step C of Example 1, starting from the compound obtained in the previous Step.

Melting point: 141-143° C.

EXAMPLE 23

4-(2-Fluoroethyl)-7-(methylsulphonyl)-3,4-dihydro-2H-1,2,4-benzothiadiazine 1,1-dioxide Step A: 4-(2-Fluoroethyl)-7-(methylsulphonyl)-4H-1,2,4-benzothiadiazine 1,1-dioxide The expected compound is obtained according to the procedure described in Steps A and B of Example 1, starting from 2-amino-5-(methylsulphonyl)-benzenesulphonamide.

Step B: 4-(2-Fluoroethyl)-7-(methylsulphonyl)-3,4-dihydro-2H-1,2,4-benzothiadiazine 1,1-dioxide The expected compound is obtained according to the procedure described in Step C of Example 1, starting from the compound obtained in the previous Step.

Melting point: 193-195° C.

EXAMPLE 24

6,7-Dichloro-4-(2,2-difluoroethyl)-3,4-dihydro-2H-1,2,4-benzothiadiazine 1,1-dioxide The expected compound is obtained according to the procedure of Example 18, replacing, in Step A, the 2-amino-5-chlorobenzenesulphonamide by the compound obtained in Step A of Example 4.

Melting point: 141-145° C.

EXAMPLE 25

7-Chloro-4-(2,2-difluoroethyl)-6-fluoro-3,4-dihydro-2H-1,2,4-benzothiadiazine 1,1-dioxide The expected compound is obtained according to the procedure of Example 18, replacing, in Step A, the 2-amino-5-chlorobenzenesulphonamide by 2-amino-5-chloro-4-fluorobenzenesulphonamide.

Melting point: 155-159° C.

EXAMPLE 26

8-Chloro-4-(2-fluoroethyl)-3,4-dihydro-2H-1,2,4-benzothiadiazine 1,1-dioxide

The expected compound is obtained according to the procedure described in Example 1, starting from 2-amino-6-chlorobenzenesulphonamide and 1-fluoro-2-iodoethane.

EXAMPLE 27

4-(2-Fluoroethyl)-7-(trifluoromethyl)-3,4-dihydro-2H-1,2,4-benzothiadiazine 1,1-dioxide The expected compound is obtained according to the procedure described in Example 1, starting from 2-amino-5-(trifluoromethyl)-benzenesulphonamide and 1-fluoro-2-iodoethane.

EXAMPLE 28

4-(2-Fluoroethyl)-7-methoxy-3,4-dihydro-2H-1,2,4-benzothiadiazine 1,1-dioxide

The expected compound is obtained according to the procedure described in Example 1, starting from 2-amino-5-methoxybenzenesulphonamide and 1-fluoro-2-iodoethane.

EXAMPLE 29

7-Chloro-4-(2,2,2-trifluoroethyl)-3,4-dihydro-2H-1,2,4-benzothiadiazine 1,1-dioxide The expected compound is obtained according to the procedure described in Example 1, starting from 2-amino-5-chlorobenzenesulphonamide and 1,1,1-trifluoro-2-iodoethane.

EXAMPLE 30

4-(2-Fluoroethyl)-3,4-dihydro-2H-1,2,4-benzothiadiazine 1,1-dioxide

The expected compound is obtained according to the procedure described in Example 1, starting from 2-aminobenzenesulphonamide and 1-fluoro-2-iodoethane.

EXAMPLE 31

7,8-Dichloro-4-(2-fluoroethyl)-3,4-dihydro-2H-1,2,4-benzothiadiazine 1,1-dioxide The expected compound is obtained according to the procedure described in Example 1, starting from 2-amino-5,6-dichlorobenzenesulphonamide and 1-fluoro-2-iodoethane.

Melting point: 230-232° C.

EXAMPLE 32

6,8-Difluoro-4-(2-fluoroethyl)-3,4-dihydro-2H-1,2,4-benzothiadiazine 1,1-dioxide The expected compound is obtained according to the procedure described in Example 1, starting from 2-amino-4,6-difluorobenzenesulphonamide and 1-fluoro-2-iodoethane.

Melting point: 146-147° C.

EXAMPLE 33

5,8-Difluoro-4-(2-fluoroethyl)-3,4-dihydro-2H-1,2,4-benzothiadiazine 1,1-dioxide The expected compound is obtained according to the procedure described in Example 1, starting from 2-amino-3,6-difluorobenzenesulphonamide and 1-fluoro-2-iodoethane.

Melting point: 118-120° C.

Pharmacological Study of Compounds of the Invention

EXAMPLE 34

Study of the Effect of Compounds on the Ionic Current Induced by AMPA in *Xenopus* Oocytes mRNA's are prepared from cerebral cortex of male Wistar rats by the caesium chloride/guanidium thiocyanate method. The poly ($A^+$) mRNA's are isolated using the PolyATtract mRNA Isolation systems kit (Promega, USA) and injected at a level of 50 ng per oocyte. The oocytes are incubated for 3 to 4 days at 18° C. to permit expression of the receptors and are then stored at 4° C. until used.

Electrophysiological recordings are carried out continuously at ambient temperature in a Plexiglass® chamber using OR2 medium (J. Exp. Zool., 1973, 184, 321-334) by the "voltage-clamp" method using two electrodes, with a third electrode placed in the bath serving as reference.

All the compounds and the AMPA are applied via the perfusion medium. (S)-AMPA is used in a concentration of 10 µM. The ionic current induced by the application of AMPA in the absence and presence of compounds is measured. For each compound studied, the concentration that doubles (EC2×) or quintuples (EC5×) the intensity of the current induced by AMPA alone (5 to 50 nA) is determined.

The compounds of the invention greatly potentiate the excitatory effects of the AMPA. By way of example, the compound of Example 1 has an EC2× of 6.7±1.4 µM and an EC5× of 14.5±0.6 µM.

EXAMPLE 35

Object Recognition in Adult Wistar Rats Aged 3 Months

The object recognition test in the Wistar rat was initially developed by ENNACEUR and DECACOUR (Behav. Brain Res., 1988, 31, 47-59). The test is based on the spontaneous exploratory activity of the animal and has the characteristics of episodic memory in humans. This memory test is sensitive to ageing (SCALL et al., Eur. J. Pharmacol., 1997, 325, 173-180) and to cholinergic dysfunctions (BARTOLINI et al., Pharm. Biochem. Behav. 1996, 53(2), 277-283) and is based on the differences in the exploration of 2 objects of fairly similar shape—one familiar, the other new. Prior to the test, the animals (male Wistar rats aged 3 months: CERJ, France) are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered. The results obtained show that the compounds of the invention greatly increase memorisation at a low dose.

By way of example, the compound of Example 1, in doses ranging from 0.03 to 1 mg/kg by the oral route, significantly improves memory retention.

EXAMPLE 36

Object Recognition in Wistar Rats Aged 17 Months

In old rats there is a deficiency in memory retention in the object recognition test. Prior to the test, the animals (male Wistar rats aged 17 months: CERJ, France) are habituated to the environment (an enclosure without an object). In the course of a first session, the rats are placed (3 minutes) in the enclosure, in which there are 2 identical objects. The duration of exploration is measured for each object. In the course of the second session (3 minutes), 1 hour later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered.

The results obtained show that the compounds of the invention, in low doses, oppose the age-related deficiency in memory retention in the object recognition test.

By way of example, in the memory retention test the compound of Example 1 significantly opposes the age-related deficiency in memory retention, even at a dose of 0.1 mg/kg by the oral route.

EXAMPLE 37

Pharmaceutical Composition

| Formula for the preparation of 1000 tablets each containing 10 mg of active ingredient: | |
| --- | --- |
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

What is claimed is:

1. A compound selected from those of formula (I):

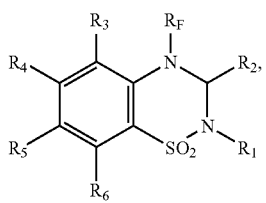

(I)

wherein:
$R_F$ represents linear or branched monofluoro- or polyfluoro-$C_1$-$C_6$alkyl or monofluoro- or polyfluoro-cycloalkylalkyl wherein the alkyl moiety is $C_1$-$C_6$ and linear or branched and the cycloalkyl moiety is $C_3$-$C_7$,
$R_1$ represents hydrogen or a group selected from linear or branched $C_1$-$C_6$alky optionally substituted by one or more halogen atoms, and linear or branched $C_1$-$C_6$alkylaminocarbonyl,
$R_2$ represents hydrogen or halogen or a group selected from linear or branched $C_1$-$C_6$alkyl optionally substituted by one or more halogen atoms, and from $C_3$-$C_7$cycloalkyl,
$R_3$, $R_4$, $R_5$ and $R_6$, which may be the same or different, each represent an atom or group selected from hydrogen, halogen, nitro, cyano, linear or branched $C_1$-$C_6$alkylsulphonyl, linear or branched $C_1$-$C_6$alkoxy, linear or branched $C_1$-$C_6$alkyl optionally substituted by one or more halogen atoms, and amino optionally substituted by one or two linear or branched $C_1$-$C_6$alkyl,
its optical isomers when they exist, and addition salts thereof with a pharmaceutically acceptable acid or base,
it being understood that $R_3$ represents hydrogen when $R_6$ does not represent hydrogen.

2. A compound of claim 1, wherein $R_F$ represents linear or branched monofluoro-$C_1$-$C_6$alkyl.

3. A compound of claim 2, wherein $R_F$ represents fluoromethyl, 2-fluoroethyl, 3-fluoropropyl or 4-fluorobutyl.

4. A compound of claim 1, wherein $R_F$ represents 2,2-difluoroethyl or 2,2,2-trifluoroethyl.

5. A compound of claim 1, wherein $R_1$ represents hydrogen.

6. A compound of claim 1, wherein $R_1$ represents linear or branched $C_1$-$C_6$alkyl optionally substituted by one or more fluorine atoms.

7. A compound of claim 1, wherein $R_2$ represents hydrogen or fluorine.

8. A compound of claim 1, wherein $R_3$ represents hydrogen.

9. A compound of claim 1, wherein $R_4$ represents hydrogen or halogen.

10. A compound of claim 1, wherein $R_5$ represents halogen.

11. A compound of claim 1, wherein $R_6$ represents hydrogen or halogen.

12. A compound of claim 1, which is 7-chloro-4-(2-fluoroethyl)-3,4-dihydro-2H-1,2,4-benzothiadiazine 1,1-dioxide.

13. A compound of claim 1, which is 6,7-dichloro-4-(2-fluoroethyl)-3,4-dihydro-2H-1,2,4-benzothiadiazine 1,1-dioxide.

14. A compound of claim 1, which is 6-chloro-7-fluoro-4-(2-fluoroethyl)-3,4-dihydro-2H-1,2,4-benzothiadiazine 1,1-dioxide.

15. A compound of claim 1, which is 6-chloro-7-bromo-4-(2-fluoroethyl)-3,4-dihydro-2H-1,2,4-benzothiadiazine 1,1-dioxide.

16. A compound selected from those of formula (VI):

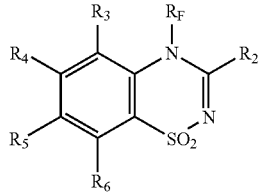

(VI)

wherein:
$R_F$ represents linear or branched monofluoro- or polyfluoro-$C_1$-$C_6$alkyl or monofluoro- or polyfluoro-cycloalkylalkyl wherein the alkyl moiety is $C_1$-$C_6$ and linear or branched and the cycloalkyl moiety is $C_3$-$C_7$,
$R_2$ represents hydrogen or halogen or a group selected from linear or branched $C_1$-$C_6$alkyl optionally substituted by one or more halogen atoms, and from $C_3$-$C_7$cycloalkyl,
$R_3$, $R_4$, $R_5$ and $R_6$, which may be the same or different, each represent an atom or group selected from hydrogen, halogen, nitro, cyano, linear or branched $C_1$-$C_6$alkylsulphonyl, hydroxy, linear or branched $C_1$-$C_6$alkoxy, linear or branched $C_1$-$C_6$alkyl optionally substituted by one or more halogen atoms, and amino optionally substituted by one or two linear or branched $C_1$-$C_6$alkyl,
its optical isomers when they exist, and addition salts thereof with a pharmaceutically acceptable acid or base.

17. A pharmaceutical composition comprising as active ingredient a compound of claim 1 in combination with one or more inert, non-toxic, pharmaceutically acceptable carriers.

18. A method of treating a living animal body, including a human, afflicted with a condition selected from anxiety and depression comprising the step of administering to the living animal body, including a human, an amount of a compound of claim 1 which is effective for alleviation of the condition.

* * * * *

UNITED STATES PATENT AND TRADEMARK OFFICE
CERTIFICATE OF CORRECTION

PATENT NO. : 7,268,129 B2 Page 1 of 1
APPLICATION NO. : 11/041495
DATED : September 11, 2007
INVENTOR(S) : Pierre Francotte et al.

It is certified that error appears in the above-identified patent and that said Letters Patent is hereby corrected as shown below:

Title Page, (30) Foreign Application Priority Data: Priority Information is missing, please add --January 26, 2004 (FR) 040400689--.

Signed and Sealed this

Fourth Day of December, 2007

JON W. DUDAS
*Director of the United States Patent and Trademark Office*